United States Patent
Xiong

(10) Patent No.: US 12,116,639 B2
(45) Date of Patent: Oct. 15, 2024

(54) MARKERS, PRIMERS, PROBES AND KIT FOR EARLY SCREENING AND DIAGNOSIS OF ENDOMETRIAL CANCER

(71) Applicant: BEIJING ORIGINPOLY BIO-TEC CO., LTD., Beijing (CN)

(72) Inventor: Sijun Xiong, Beijing (CN)

(73) Assignee: BEIJING ORIGINPOLY BIO-TEC CO., LTD., Beijing (CN)

( * ) Notice: Subject to any disclaimer, the term of this patent is extended or adjusted under 35 U.S.C. 154(b) by 0 days.

(21) Appl. No.: 17/883,872

(22) Filed: Aug. 9, 2022

(65) Prior Publication Data
US 2023/0076141 A1 Mar. 9, 2023

Related U.S. Application Data

(63) Continuation of application No. PCT/CN2022/095439, filed on May 27, 2022.

(30) Foreign Application Priority Data

Aug. 5, 2021 (CN) .......................... 202110898883.2
Oct. 21, 2021 (CN) .......................... 202111228571.7

(51) Int. Cl.
*C12Q 1/6886* (2018.01)
*C12Q 1/6858* (2018.01)

(52) U.S. Cl.
CPC ......... *C12Q 1/6886* (2013.01); *C12Q 1/6858* (2013.01); *C12Q 2600/154* (2013.01); *C12Q 2600/16* (2013.01)

(58) Field of Classification Search
None
See application file for complete search history.

(56) References Cited

U.S. PATENT DOCUMENTS

| 2014/0212873 A1* | 7/2014 | Godler | G16B 30/00 702/19 |
| 2015/0065379 A1* | 3/2015 | Sanyal | A61B 10/0045 600/580 |
| 2022/0244263 A1* | 8/2022 | Graeber | A61K 45/06 |

FOREIGN PATENT DOCUMENTS

| CN | 109069670 A | 12/2018 | |
| CN | 110387420 B | 11/2020 | |
| WO | WO-2013148147 A1 * | 10/2013 | ........... C12Q 1/6886 |

OTHER PUBLICATIONS

Laird et al. (PNAS 2004 Vol 101 p. 204-209) (Year: 2004).*
Huang et al. "Integrated Epigenomics Analysis Reveals a DNA Methylation Panel for Endometrial Cancer Detection Using Cervical Scrapings." Clinical Cancer Research 23(1) (2016): 263-272.
Liew et al. "Combined genetic mutations and DNA-methylated genes as biomarkers for endometrial cancer detection from cervical scrapings.", Clinical Epigenetics 11(1): 170 (2019).

* cited by examiner

Primary Examiner — Katherine D Salmon
(74) Attorney, Agent, or Firm — Nixon Peabody LLP; Mark J. FitzGerald; Alissa R. Young

(57) ABSTRACT

The present invention discloses markers, primers, probes and a kit for early screening and diagnosis of endometrial cancer. The markers are partial methylated regions in the four genes of CDO1, CELF4, HAND2 and HS3ST2. Detection primers and probes are designed for these methylated regions and to have clasp structures. The kit includes the aforementioned primers and probes. The present invention screens and combines multiple methylated regions to determine the most suitable methylated position for combined diagnosis, which can significantly improve the sensitivity and specificity of the detection for early endometrial cancer. The kit is especially suitable for early screening and diagnosis of endometrial cancer with cervical exfoliated cells as a sample. Even if the DNA template concentration is low, endometrial cancer can be detected. The kit has the advantages of non-invasive sampling, fast detection speed, higher sensitivity and specificity, etc., and can ensure the accuracy of the results to help achieve the purpose of early detection, early diagnosis, and early treatment of endometrial cancer.

18 Claims, 5 Drawing Sheets

Specification includes a Sequence Listing.

MARKERS, PRIMERS, PROBES AND KIT FOR EARLY SCREENING AND DIAGNOSIS OF ENDOMETRIAL CANCER

CROSS-REFERENCE TO RELATED APPLICATIONS

This application claims benefit to International Patent Application No. PCT/CN2022/095439 filed on May 27, 2022 which claims benefit under 35 U.S.C. § 119(b) of CN Application No. 202110898883.2 filed on Aug. 5, 2021 and CN Application No. 202111228571.7 filed Oct. 21, 2021, the contents of each of which are incorporated herein by reference in their entireties.

SEQUENCE LISTING

The instant application contains a Sequence Listing which has been submitted in XML format via Patent Center and is hereby incorporated by reference in its entirety. Said XML copy, created on Oct. 5, 2022, is 070019-192420US-PX_SL.xml and is 42,712 bytes in size.

TECHNICAL FIELD

The invention relates to the technical field of nucleic acid in vitro diagnosis, in particular to the use of specific gene methylation markers in early screening and early detection of endometrial cancer, in particular to markers, primers and kits for early screening and diagnosis of endometrial cancer.

BACKGROUND ART

Endometrial cancer is an epithelial malignant tumor that occurs in the endometrium, has a high incidence in people of 50-60 years old, is more common in postmenopausal women and has younger trend in recent years. According to the latest global cancer data report, the number of new cases of female endometrial cancer worldwide in 2020 reached 420,000, ranking sixth in the incidence of female malignant tumors worldwide. In 2020, the number of new cases of female endometrial cancer in China is 80,000, ranking ninth in the incidence of female malignant tumors in China. In the United States, endometrial cancer is the fourth most common cancer after breast, lung, and colorectal cancer. The lesion is confined to the uterus when discovered in approximately 70% of patients with endometrioid cancer. In most cases, endometrial cancer is localized lesion, and the survival rate is relatively high, but symptoms such as early irregular vaginal bleeding and vaginal discharge are often ignored, and the opportunity for early diagnosis is lost. Data show that the rate of increase for the mortality of endometrial cancer in China has exceeded the rate of increase for the incidence in recent years. The increased mortality may be related to the increase in advanced cases, high-risk pathological types (such as uterine papillary serous carcinoma), and advanced age at the time of diagnosis. The surveillance, epidemiology, and outcome (SEER) data in the United States show that young patients, early cases, and patients with low-grade disease have better survival rates.

The endometrial cancer in most of the patients with endometrial cancer is sporadic, but hereditary in about 5% of the patients with endometrial cancer, which is characterized by the age of onset of these patients is 10-20 years younger than the average age of patients with sporadic endometrial cancer. Female with Lynch syndrome is a high-risk group of endometrial cancer, with an incidence as high as 60%. It is recommended that patients with Lynch syndrome to closely monitor the endometrium.

According to the current guidelines for the diagnosis and treatment of endometrial cancer, the current clinical methods for early detection of endometrial cancer mainly use vaginal ultrasound, serum tumor marker CA125, cytological detection based on endometrial cell samplers, and histopathological methods for final confirmed diagnosis: diagnostic curettage and hysteroscopic biopsy. It is reported in the literature that endometrial cancer has certain ultrasound characteristic images. As long as one is proficient in the diagnostic techniques and image features of ultrasound for endometrial cancer, ultrasound is still of great value in the diagnosis of endometrial cancer, but the sensitivity of ultrasound diagnosis to early endometrial cancer is not high. For ultrasound diagnosis of endometrial cancer, the sensitivity is 59.4%, the specificity is 81.1%, the false negative rate is 40.6%, and the false positive rate is 18.9%. The detection of serum CA125 has certain value in the early diagnosis of endometrial cancer and prediction of prognosis. However, the positive rates of serum CA125 in patients with endometrial cancer and benign uterine lesions are 24% and 20%, respectively. Therefore, the detection of serum CA125 lacks sensitivity for early diagnosis of endometrial cancer, and has relatively poor specificity. Endometrial cells are not easy to fall off outside the menstrual period, while cancer cells that fall off the uterine cavity are prone to dissolution and degeneration, and are difficult to identify after staining Therefore, the positive rate of vaginal exfoliative cytology is not high. Endometrial cell harvester combined with liquid-based cytology section technique is commonly used for early detection of endometrial cancer. For the diagnosis of endometrial atypical hyperplasia, the sensitivity is 55% and the specificity is 82.6%, and for the diagnosis of endometrial cancer, the sensitivity is 36.4%, and the specificity was 99.7%. Therefore, liquid-based cytologic test using materials obtained by the endometrial cell harvester can be used to screen symptomatic population and high-risk population for endometrial lesions, but the sensitivity for the diagnostic technique in the cytologic test process is poor, and sampling is somewhat traumatic. Diagnostic curettage and hysteroscopic biopsy are necessary methods for a confirmed diagnosis of endometrial cancer. In view of the fact that endometrial biopsy may have about 10% false negatives, if endometrial cancer is highly suspected or has typical symptoms, patients with negative endometrial biopsy should be diagnosed again under anesthesia with fractional curettage and cervical canal scratching to reduce missed diagnosis. For patients with persistent or repeated vaginal bleeding with unclear endometrial lesions, auxiliary hysteroscopy can help determine the benign or malignant endometrial lesions, but is harmful to the human body and is not suitable for early screening of endometrial cancer and thus can only be used for the final pathological diagnosis. Therefore, an objective, reproducible, and highly specific detection method is needed to better identify the possibility of endometrial cancer. At present, there is still a lack of effective screening methods for endometrial cancer, and non-invasive screening methods can be explored. At present, the incidence of endometrial cancer in China is increasing every year, and new screening methods are urgent.

DNA methylation is a type of epigenetics and is the covalent modification of cytosine at the 5' end of DNA. This modification is usually related to gene silencing. Because DNA methylation can remain relatively stable for a long time, and at the same time exist in samples (such as paraffin sections), DNA methylation has become the most useful apparent marker for human disease research. In the research and application related to early screening, methylation marker detection is currently generally recognized as the most feasible detection scheme, because DNA methylation markers have better stability than mRNA, protein or metabolite markers, and such stability facilitates stable detection; compared with DNA markers, methylation markers have better diversity and can reflect the influence of changes in the internal and external environment of the body. Methylation is a modification on DNA that finely regulates gene transcription, basically showing that hypermethylation reduces gene expression, and hypomethylation increases gene expression. Changes in the level and pattern of methylation will cause the expression of tumor suppressor genes to be turned off or the expression of proto-oncogenes to be activated. Therefore, the detection of DNA methylation levels at specific sites can be used to predict the growth of tumors in individuals, thereby achieving the goal of early screening and early diagnosis for tumors.

In recent years, DNA methylation has attracted more and more attention from basic research and clinical transformation. A large number of pathways have been found to be regulated by epigenetics, the generation of big data for methylation based on chip technology and next-generation sequencing technology, and changes in DNA methylation levels in body fluids demonstrated by many existing studies can be used for early diagnosis, prognosis evaluation and therapeutic efficacy evaluation of cancers; some cutting-edge work has begun to be transformed and entered clinical applications. DNA methylation has been applied to the clinic in the early screening and early diagnosis of bowel cancer, represented by Cologuard from Exact Sciences in the United States and New Horizon Health and Creative Biosciences in China. For early screening and early diagnosis for tumors in terms of DNA methylation in other types of cancers, although there are also domestic and foreign companies conducting related research, the overall research is still in the scientific research stage, and there are few that can be applied to the clinic and have confirmed diagnostic value. Among them, the American company Foundation Medicine has conducted scientific research on some data in the direction of multi-solid tumor (lung cancer, breast cancer, stomach cancer, esophageal cancer, colorectal cancer, liver cancer, bile duct and gallbladder cancer, pancreatic cancer, gastrointestinal stromal tumor, head and neck cancer, cervical cancer, ovarian cancer, endometrial cancer, prostate cancer, bladder cancer, kidney cancer, melanoma, etc.) methylation. In 2016, Huang et al. screened 180 related genes with 50 cases of endometrial cancer, 40 cases of uterine fibroids, and 56 cases of healthy people's cervical secretions as the research objects, and found that 14 of them were hypermethylated in endometrial cancer. Among them, three genes, BHLHE22, CDO1 and CELF4 were particularly prominent and had a sensitivity between 83.7%-96% and a specificity up to 78.7%-96.0%. When testing in pairs, the sensitivity can reach 91.8% while the specificity can be maintained at 95.5%. In 2014, Nicolas et al. collected 148 endometrial cancer samples and 23 benign endometrial samples, studied 1500 probes covering 807 genes, and screened out 8 potential genes (ADCYAP1, ASCL2, HS3ST2, HTR1B, MME, NPY, and SOX1) which had the potential to distinguish benign and malignant endometrium. In 2013, Allison et al. studied the methylation of 27,000 CpG islands in 64 endometrial tissue samples and 23 control samples, and found that the HAND2 gene was one of the most common hypermethylated genes in endometrial cancer. At the same time, in a follow-up study with 272 women, the role of HAND2 was once again proven. The methylation of this gene is one of the important factors in the development of endometrial lesions.

DNA methylation mainly occurs in the promoter region of a gene, and is usually closely related to the inactivation of the expression of a tumor suppressor gene. The main methods currently used in the detection for gene methylation include: methylation-specific PCR (MSP), bisulfite sequencing PCR (BSP) and high resolution melting (HRM) etc. Methylation-specific PCR mainly relies on the binding of primers with target templates for PCR amplification to detect methylated sites; the bisulfite sequencing PCR relies on sequencing primers for PCR amplification, and subsequent sequencing is performed on this basis to realize the detection of methylated sites; the high-resolution melting distinguishes between methylated and non-methylated status mainly through the change of the melting temperature caused by the change of the CG content in the sample. Each method has its own characteristics. The BSP has high accuracy and is easy for intuitive interpretation, but has low sensitivity, relatively more cumbersome operation, and high cost; the HRM method has relatively low sensitivity, and has slightly complicated analysis for the results; the MSP has high detection sensitivity and relatively low requirements for samples, at the same time, has short detection time, has low cost, and has results easy to interpret.

Non-invasiveness and low cost are ideal features for early cancer screening. For the detection of endometrial cancer, vaginal ultrasound, or cytological detection based on endometrial cell samplers and diagnostic curettage, etc. are mainly used clinically. On one aspect, the detection sensitivity is low, and on another aspect, the direct collection of endometrial cells has a certain degree of invasiveness.

In view of this, the present invention is proposed.

SUMMARY OF THE INVENTION

The purpose of the present invention is to address the above-mentioned shortcomings in the prior art and provide a markers, primers, probes and kits for early screening and diagnosis of endometrial cancer, the markers, primers, probes and kits have high detection accuracy, are convenient and fast to operate, and can provide a reliable reference for the clinical diagnosis of endometrial cancer. Cervical exfoliated cells can be used as a test sample, which would not cause damage to the patient and is easier to be accepted by the patient.

The specific technical scheme of the present invention is described in detail as follows:

in the first aspect, the present invention provides a set of markers for early screening and diagnosis of endometrial cancer, selected from at least any one of the following methylated regions in each of the target genes CDO1, CELF4, HAND2, and HS3ST2:

CDO1 gene: Chr5:115816884-115817037, Chr5: 115816018-115816152, Chr5: 115815760-115815872;

CELF4 gene: Chr18:37566573-37566662, Chr18: 37565524-37565639, Chr18:37565036-37565173;

HAND2 gene: Chr4:173530858-173530953, Chr4: 173530225-173530335, Chr4: 173528847-173528958;

HS3ST2 gene: Chr16:22813813-22813928, Chr16: 22814029-22814146, Chr16: 22814452-22814557.

Through combined screening for the types of endometrial cancer-related genes and the methylated region of each gene, the above four marker genes (or target genes) and their corresponding functional optimal methylated regions are finally screened out. The interpretation threshold can be determined by the complementarity of the methylation results for each marker gene. When the results for each methylated region are combined with each other for the early detection of endometrial cancer, the accuracy of the detection result is so high that can provide clinicians with auxiliary diagnostic reference.

Optionally or preferably, the above-mentioned markers for early screening and diagnosis of endometrial cancer are selected from the following methylated regions in each of the target genes CDO1, CELF4, HAND2, and HS3ST2:
CDO1 gene: Chr5:115815760-115815872;
CELF4 gene: Chr18:37565524-37565639;
HAND2 gene: Chr4:173528847-173528958;
HS3ST2 gene: Chr16:22813813-22813928.

The above-mentioned combination has the best detection effect.

In the second aspect, the present invention also provides a set of detection primers for early screening and diagnosis of endometrial cancer, the detection primers are used to detect the methylation status of the methylated regions in the above-mentioned marker genes correspondingly. The primer design adopts a clasp structure. A sequence of 5-10 bp in length which is complementary to and paired with the 3' end and contains no CG site is added at the 5' end of the nucleotide sequence of the primers. The terminal last two bases at the 3' end are CG. The Tm value of the double-stranded binding region in the primers should be consistent with the annealing temperature in the PCR reaction system.

In the above primer design, the added sequence of 5-10 bp in length contains no CG site and can ensure tighter binding when forming the clasp. The primer sequence adopts a clasp design structure. First, there is no primer dimer produced. During the annealing process, the primer preferentially makes itself a double-stranded structure and does not form a double-stranded structure with other primers, so the primer dimer would not form. Secondly, there is a high specificity. Because the primer itself has a clasp structure, the free energy of binding between the primer and the methylated target sequence needs to be greater than the ring free energy formed by the primer itself, so when there is a mismatched base at the 3' end of the primer, the primer containing the clasp structure is almost difficult to bind to an unmethylated sequence, and better specificity for primer amplification is maintained. Thirdly, there is a high sensitivity, because the sample used is cervical exfoliated cells, the amount of DNA template is small, the content of methylated DNA in the template is low and the primer designed with a clasp structure would only match the methylated target sequence uniquely. The amplification efficiency of the primer is greatly improved. There is no need to add other additional modifications during the design and synthesis of the primer, the synthesis is simple, and can be completed only by a commonly used synthesizer.

The above-mentioned primers maintain a high specificity for primer amplification due to the clasp design structure, so the amplification efficiency between the primers would not interfere, and this is an obvious advantage for the amplification of multiple primers. The present invention adopts 4 target genes plus one internal reference gene to perform amplification in a reaction system, and there is no mutual influence on the amplification efficiency between the primers for each gene.

Optionally or preferably, the above-mentioned detection primers for early screening and diagnosis of endometrial cancer have the nucleotide sequences as follows:
in the CDO1 gene:
the detection primers corresponding to Chr5: 115816884-115817037 are SEQ ID NO: 1-2,
the detection primers corresponding to Chr5:115816018-115816152 are SEQ ID NO: 4-5,
the detection primers corresponding to Chr5:115815760-115815872 are SEQ ID NO: 7-8;
in the CELF4 gene:
the detection primers corresponding to Chr18:37566573-37566662 are SEQ ID NO: 10-11,
the detection primers corresponding to Chr18:37565524-37565639 are SEQ ID NO: 13-14,
the detection primers corresponding to Chr18:37565036-37565173 are SEQ ID NO: 16-17;
in the HAND2 gene:
the detection primers corresponding to Chr4:173530858-173530953 are SEQ ID NO: 19-20,
the detection primers corresponding to Chr4:173530225-173530335 are SEQ ID NO: 22-23,
the detection primers corresponding to Chr4:173528847-173528958 are SEQ ID NO: 25-26;
in the HS3ST2 gene:
the detection primers corresponding to Chr16: 22813813-22813928 are SEQ ID NO: 28-29,
the detection primers corresponding to Chr16: 22814029-22814146 are SEQ ID NO: 31-32,
the detection primers corresponding to Chr16: 22814452-22814557 are SEQ ID NO: 34-35.

In the third aspect, the present invention also provides a set of detection probes for early screening and diagnosis of endometrial cancer, the detection probes are used to detect the marker genes in claim 1 correspondingly. The design of the nucleotide sequence of the detection probes adopts a clasp structure. A sequence of 3-6 bp in length which is complementary to and paired with the terminal 3-4 bp region near the 3' end and contains no CG site is added at the 5' end of the nucleotide sequence. The Tm value of the double-stranded binding region in the probes should be 2-15° C. higher than the annealing temperature in the PCR reaction system. The free energy of binding between the nucleotide sequence of the probes and the sequence of the marker genes is higher than that for the clasp structure formed by the probes themselves; the 5' end of the detection probes is labeled with a fluorescent group, and the 3' end is labeled with a quenching group, and different detection probes for marker genes in the same detection system are labeled with different fluorescent groups.

The fluorescent groups include, but is not limited to, FAM, ROX, CY5 and HEX, and the quenching groups include but are not limited to BHQ1 and BHQ2.

The detection probes for target genes labeled with the different fluorescence groups can be put in one tube for reaction to ensure the best amplification efficiency of different target genes in the sample. The fluorescence curve is a standard S-shaped amplification curve, and the fluorescence curve keeps the same trend with the single amplification curve of each gene.

The design of the probe also adopts a clasp design structure, which can make the fluorescent group and the quenching group close, and there would be no fluorescence when the probe forms a ring structure. At the same time, the probe sequence contains 2-5 CG sites for specific recognition of methylated sequences. A sequence of 3-6 bp in length which is complementary to the base sequence of the terminal 3-4 bp region near the 3' end is added at the 5' end of the probe to form a complementary region which contains no CG site. The Tm value of the double-stranded binding region in the probe is 2-5° C. higher than the annealing temperature in the reaction system. With the increase of CG sites, the Tm value needs to be increased by 5-10° C., and the specific needs are determined according to the screening result for the probe. In the process of designing the probe, the free energy of binding between the probe sequence and the target sequence is higher than that for the clasp structure formed by the probe sequence itself.

The advantages of this probe design are: First, due to the formation of the clasp structure, the fluorescent group and the quenching group of the sequence are closer, the fluorescence quenching effect is better, and no additional fluorescence is generated, so the fluorescence background is low. Secondly, there is a high specificity. On one aspect, the probe has a clasp design structure, and the sequence itself is difficult to bind to unmethylated sequences. On another aspect, the probe contains 2-5 CG sites to ensure that this probe sequence would only bind to matching methylated sequences. Thirdly, there is a high sensitivity. When the probe ring structure is opened and binds to the methylation sequence and the fluorescent group is separated from the quenching group, then the fluorescence can be detected. Fourth, the design is suitable for multiple amplification reactions. Each of the probe sequences forms a clasp structure. It is difficult to perform complementary pairing and binding with each other. Thus, the primer dimer would not be produced, and the binding of the probe sequence and the target sequence would not be affected.

Optionally or preferably, the above-mentioned detection probes for early screening and diagnosis of endometrial cancer have the nucleotide sequences as follows:
    CDO1 gene detection probe: SEQ ID NO: 9
    CELF4 gene detection probe: SEQ ID NO: 15
    HAND2 gene detection probe: SEQ ID NO: 27
    HS3ST2 gene detection probe: SEQ ID NO: 30.

In the fourth aspect, the present invention provides a detection kit for early screening and diagnosis of endometrial cancer, which includes any of the detection primers described above, and any of the detection probes described above.

Optionally or preferably, in the above-mentioned detection kit for early screening and diagnosis of endometrial cancer, detection primers and detection probe for an internal reference gene are further included; the internal reference gene is GAPDH; the nucleotide sequences of the detection primers for the internal reference gene are shown in SEQ ID NO: 37-38, and the nucleotide sequence of the detection probe for the internal reference gene is shown in SEQ ID NO: 39, the 5' end of the nucleotide sequence of the detection probe for the internal reference gene is labeled with a fluorescent group and the 3' end is labeled with a quenching group; in the same detection system, the fluorescent group for labeling the detection probe of the internal reference gene is different from the fluorescent group for labeling the detection probe of the marker gene.

Optionally or preferably, the above-mentioned detection kit for early screening and diagnosis of endometrial cancer further includes a PCR reaction solution and a methylation pretreatment reagent for a sample; the sample is cervical exfoliated cells, and the methylation pretreatment reagent for the sample includes a cell genomic DNA extraction reagent and a DNA bisulfate conversion reagent.

Sample pretreatment is of great importance to the entire kit, and is directly related to the subsequent PCR amplification effect.

The kit is especially suitable for exfoliated cervical cells as a sample. At present, the commonly used clinical sampling method is to collect endometrial samples based on the endometrial cell sampler or obtain endometrial tissue through curettage. This sampling method is invasive to the patient and would bring certain trauma to the patient. The above kit uses a sample of cervical exfoliated cells, and also detects cells that have fallen from the endometrial area to the cervix, therefore, the amount of endometrial cells is very low, but the sample source is simpler, and the sample is easy to take without invasiveness. Since the amount of endometrial cells in cervical exfoliated cells is low, correspondingly, the sample pretreatment reagent and the subsequent PCR reaction solution included in this kit are particularly important to determine whether DNA methylation changes in endometrial cells can be detected.

When using the above methylation pretreatment reagent for a sample, there are two processes, one is the extraction process of genomic DNA, and the other is the conversion process of bisulfite. If one of the processes fails, the final result will change greatly.

The cell genomic DNA extraction reagent uses cervical exfoliated cells as a sample. Preferably, the genomic DNA extraction kit (nucleic acid extraction or purification reagents (Beijing OriginPoly Bio-Tec Co., LtD., Beijing Large-scale Medical Equipment Record No. 20210020)) independently developed by the applicant is used to extract DNA from cervical exfoliated cells. This extraction/purification kit has been greatly improved in terms of DNA yield and DNA purity through comparative screening during the development process. 2 mL cervical exfoliated cell preservation solution is extracted. The total amount of DNA is between 4 μg-8 μg, and the OD260/280 is between 1.9-2.0, maintaining a good yield and purity.

After the DNA extraction is completed, the DNA bisulfite conversion experiment needs to use DNA bisulfite conversion reagent. It is also preferred to use the bisulfite conversion kit (methylation detection sample pretreatment kit (Beijing OriginPoly Bio-Tec Co., LtD., Beijing Large-scale Medical Equipment Record No. 20200110)) independently developed by the applicant. The main indicators of the conversion process are compared: one indicator is the conversion rate of bisulfite, that is, how much C in the sequence can be converted into U; another indicator is the purification efficiency after conversion, that is, what is the final bisDNA yield. When the above-mentioned DNA bisulfite reagent is used, the conversion efficiency of 99.8% and the purification efficiency of 99% for bisulfite provides high-quality bisDNA for subsequent PCR amplification reactions.

Optionally or preferably, in the above-mentioned detection kit for early screening and diagnosis of endometrial cancer, each one-person-portion of the PCR reaction solution is composed of 0.5-1 μL of methylation-specific Taq DNA polymerase at a concentration of 1 U/μL, 2-5 μL of dNTPs at a concentration of 10 mM, 2-6 μL of $Mg^{2+}$ at a concentration of 2-5 mM, 5 μL of 10×DNA polymerase buffer and purified water made up to 15 μL.

In the above PCR reaction system, the important component is the methylation-specific Taq polymerase, which has the following advantages: the template sequence after the conversion of bisulfite is amplified, the sequence after the conversion can be specifically recognized, and the amplification efficiency of the primers on the sequence after the conversion is improved. Insufficient amount of enzyme would reduce the amplification efficiency, and too much enzyme amount would easily cause non-specific amplification, so the amount of enzyme can significantly affect the subsequent PCR amplification results. In addition, the ratio of dNTPs, $Mg^{2+}$ and 10×DNA polymerase buffer in the system is also directly related to the amplification efficiency of the combination of the primers and the probes.

The PCR reaction system is specifically aimed at bis-DNA amplification after bisulfite conversion and contains multiple primers and probes. Therefore, the choice of PCR reaction solution is particularly important. The amplification efficiency of each gene primer and probe in the system should be similar to that of its corresponding single-plex amplification to ensure that the primers or probes in the system do not interfere with each other, and give full play to the amplification effect of each set of primers and probes. It is necessary to screen and verify different methylation-specific Taq polymerases and their ratios with other components to ensure the best amplification efficiency of the entire multiplex amplification system.

Compared with the prior art, the present invention has the following beneficial effects:

1. The present invention screens out four marker genes (target genes, genes of interest) CDO1, CELF4, HAND2 and HS3ST2, and determines the optimal methylated region in each gene. The methylated region can be combined with each other for early detection of endometrial cancer. The selected regions include not only the promoter region of the gene, but also the coding region of the gene. Due to the diversity of endometrial cancer, the combined detection of methylated regions of multiple genes which are complementary between functions is selected to significantly improve the sensitivity of the detection of endometrial cancer, but has high specificity for normal and benign endometrial tumors. The detection composition detects patients with possible gynecological malignant tumors early through molecular epigenetic methods using methylation detection technology, and the result is very accurate, and can provide clinicians with auxiliary diagnostic reference for early preventive treatment.

2. Detection primers and probes are designed for specific methylated sites of the combined four marker genes. The primers and probes all adopt clasp design structures and can dual-recognize the methylated template. The sensitivity and specificity of detection are significantly improved, the accuracy of detection is increased, and the error of detection is reduced. For cases where cervical exfoliated cells are used as samples, the amount of DNA is small, and the amount of DNA methylation is less, it is very important to improve sensitivity. Using the primers and probes of the present invention, accurate detection results can be obtained with a small amount of samples. This is more suitable for clinical applications.

All detection systems composed of the primers and probes can also use multi-gene multi-channel fluorescence detection methods, use five fluorescent probe labels and accurately recognize methylated sequences through specific primer and probes, and use optimized special methylation DNA Taq polymerase, to accurately detect methylated sites in CDO1, CELF4, HAND2 and HS3ST2 genes and complete detection of methylated sites in multiple genes in batches. The detection method is simple to operate and intuitive to interpret, and results can be obtained within 8 hours. Universal fluorescence quantitative PCR instrument can meet the detection needs. The entire experimental process adopts a one-stop fully enclosed form, which is easier to operate and avoids the possibility of cross-contamination.

3. The methylation pretreatment reagent for a sample and PCR reaction solution in the kit respectively provide guarantee for the DNA extraction and pretreatment of cervical exfoliated cells and the subsequent PCR reaction. At present, there are many phenomena of non-specific amplification (false positive results) in PCR amplification. At present, the most mainstream bisulfite conversion technology performs conversion on the extracted samples. Limited by the limitations of current bisulfite conversion technology, in addition to about 80% of the target genome may be lost, there would also be a certain probability of unconverted templates. These are the reasons that may cause false positive results. In the present invention, in addition to adopting clasp structures in the design of the primers and probes for target genes and increasing the sensitivity and specificity of amplification, the pretreatment (including DNA extraction and bisulfite conversion) of sample methylation has also been optimized to improve the final bisDNA conversion yield.

4. The kit combines specific primers and probes, sample pretreatment reagents, DNA polymerase in the PCR reaction solution, etc., to ensure that the kit maintains high sensitivity when used, the primers and probes have good specificity, the amplification efficiency is high, there is also a very good detection rate for low-concentration templates, and there is a very high sensitivity for the detection of early endometrial cancer. The high sensitivity of this kit is suitable for early detection of endometrial cancer.

DETAILED DESCRIPTION OF EMBODIMENTS

Figure 1:
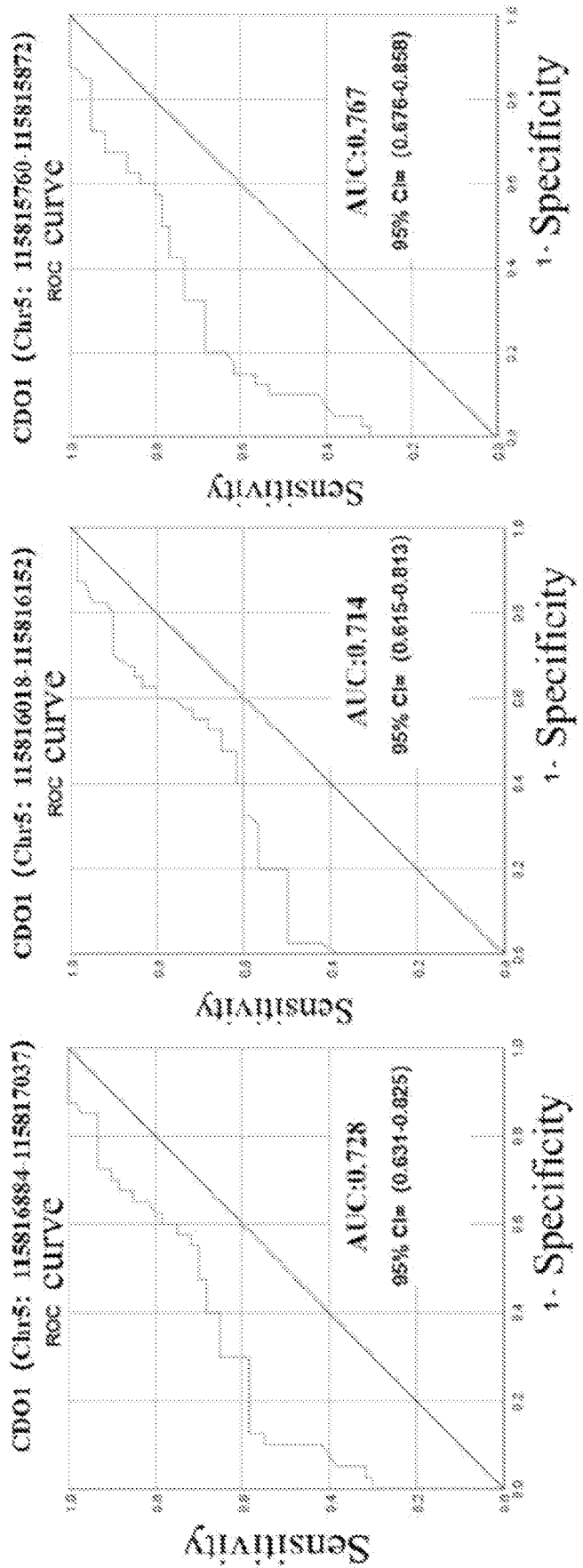
FIG. 1 shows the ROC curve of the methylated regions screened for each gene of CDO1, CELF4, HAND2 and HS3ST2.
Figure 1:
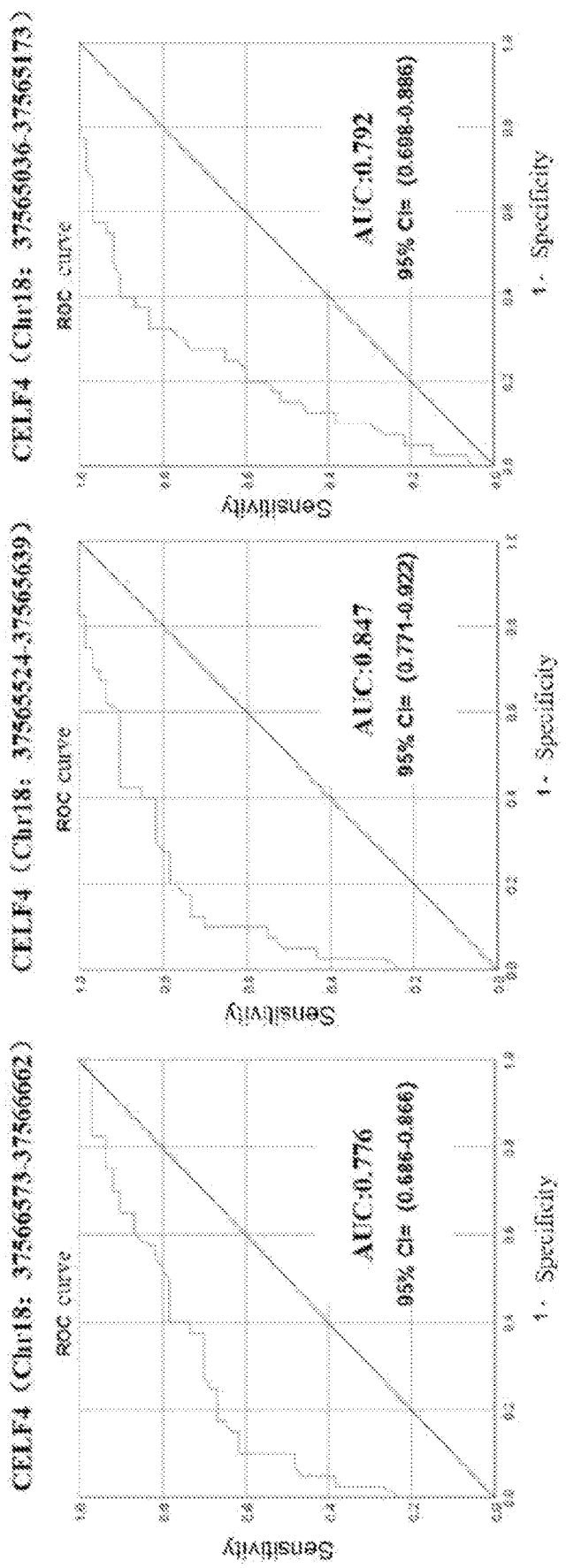
Figure 1:
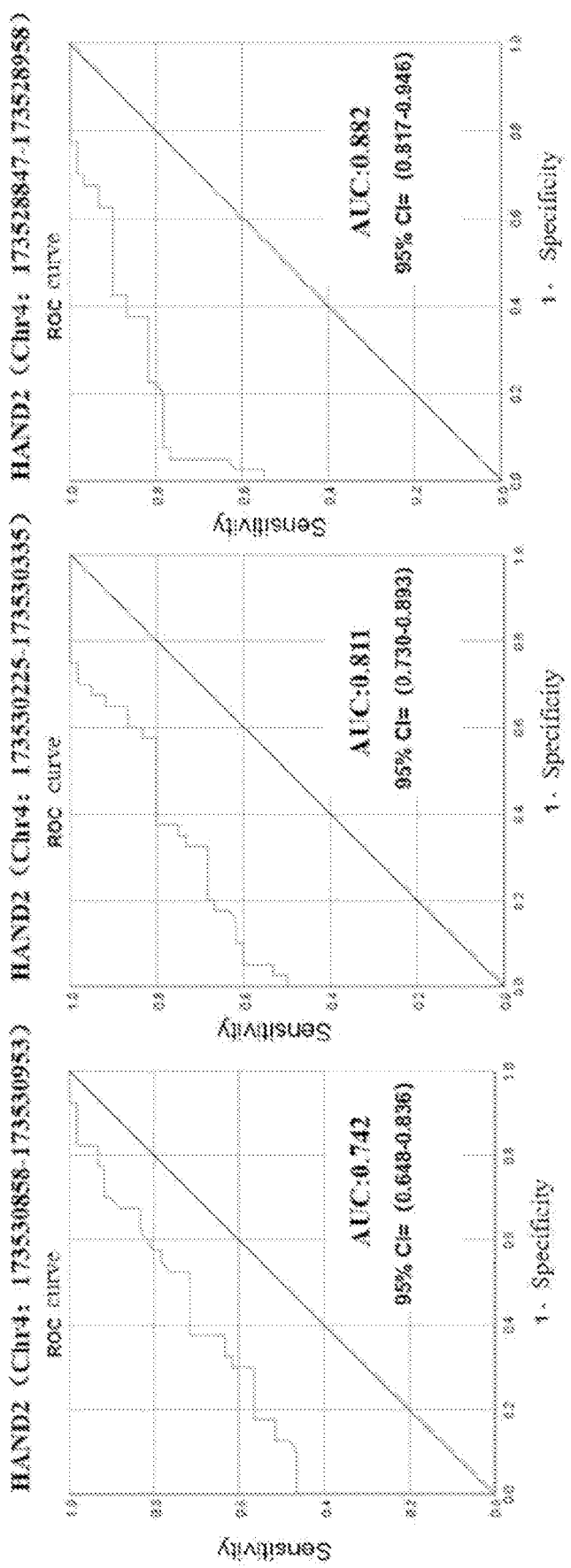
Figure 1:
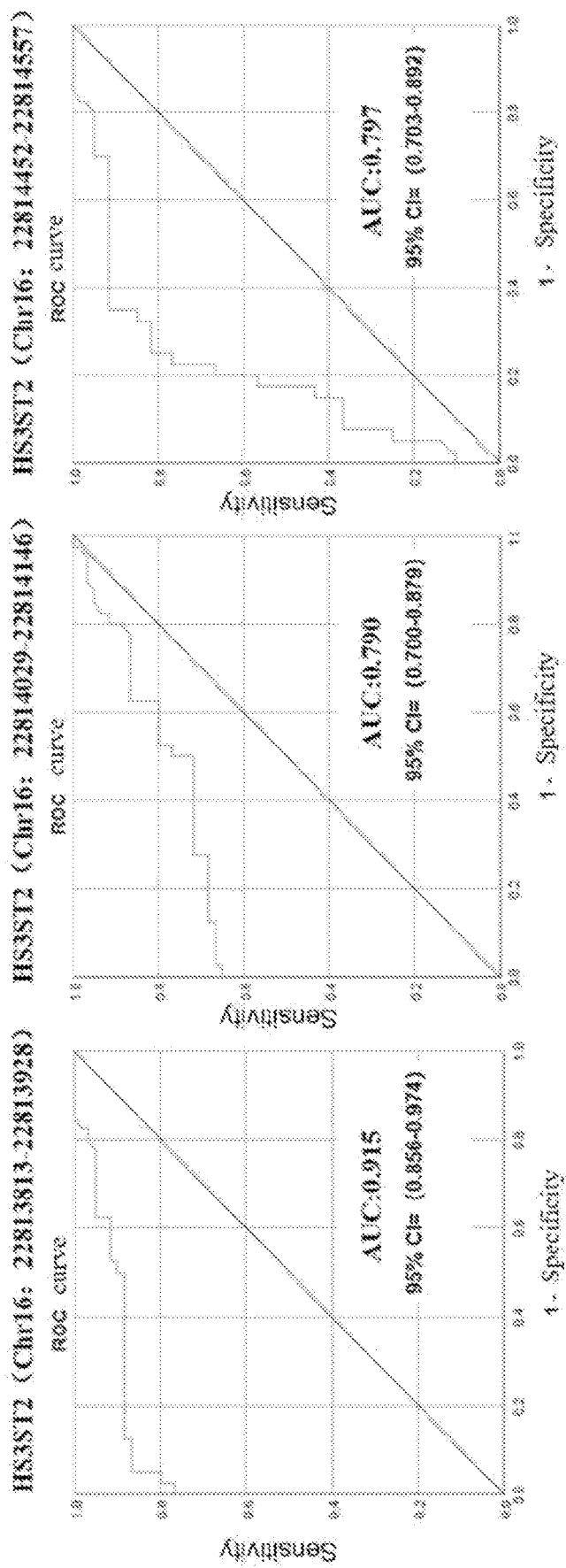
Figure 2:
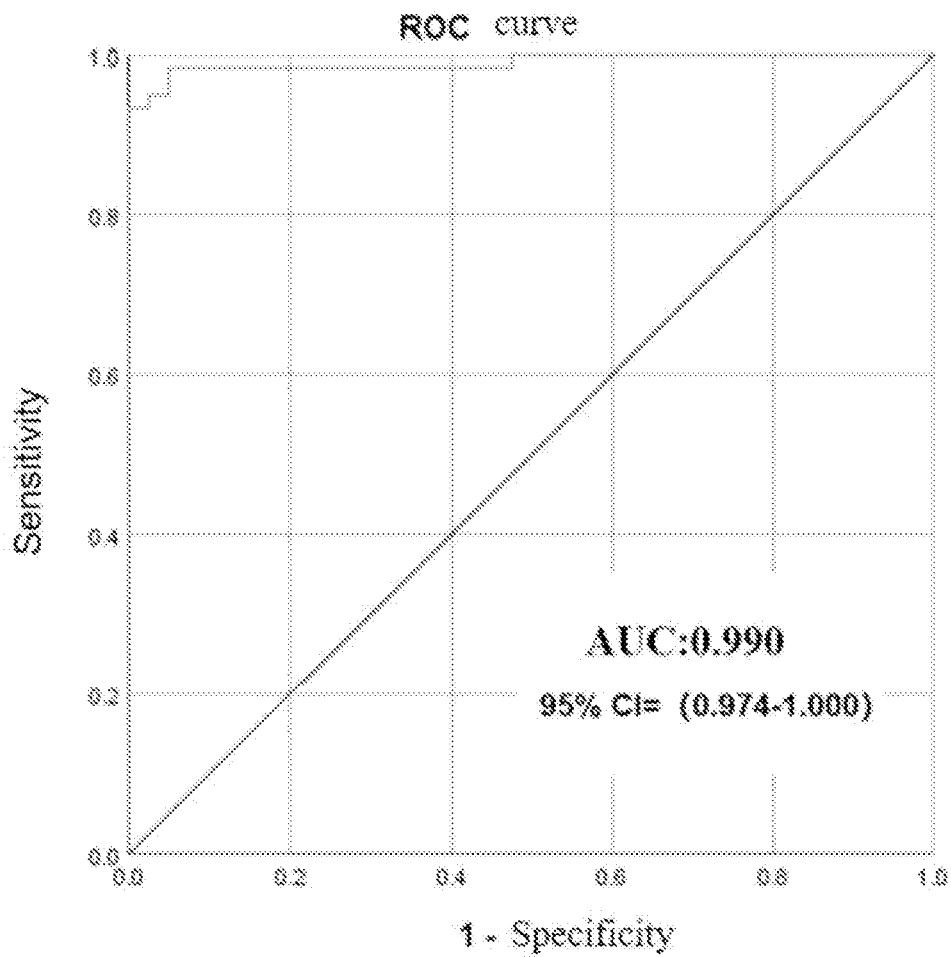
FIG. 2 shows the ROC curve of CDO1, CELF4, HAND2 and HS3ST2 in combined detection.

The technical solutions of the present invention will be explained and described in detail below in conjunction with the preferred specific embodiments in accordance with the drawings, so that those skilled in the art can better understand and implement the present invention.

Example 1

Detection test of kit for detecting the methylation in endometrial cancer-related genes CDO1, CELF4, HAND2 and HS3ST2.

The specific nucleotide sequences of the primers and probes used are shown in the following table:

| CDO1-F1  | ctaaatTTTTTTTTTTTTTTATTTAGCG    | SEQ ID NO: 1 |
|----------|---------------------------------|--------------|
| CDO1-R1  | ttaaagtgTCTCTCCCCCACTTTAACG     | SEQ ID NO: 2 |
| CDO1-FP1 | FAM-tataatTAGCGTCGCGAATTATA-BHQ1| SEQ ID NO: 3 |
| CDO1-F2  | aaccaaGTTTAAAGTGATTGGTTCG       | SEQ ID NO: 4 |
| CDO1-R2  | aaggtCCAATAAAATCCACCTTCCG       | SEQ ID NO: 5 |

-continued

| | | |
|---|---|---|
| CDO1-FP2 | FAM-acccTTAGTCGCGGGGTTGGT-BHQ1 | SEQ ID NO: 6 |
| CDO1-F3 | ataacGTTTATATTTTTAAGTTATCG | SEQ ID NO: 7 |
| CDO1-R3 | gattagACCCTCTACTAATCCG | SEQ ID NO: 8 |
| CDO1-FP3 | FAM-catctATTTCGGGCGCGGAGATGCGG-BHQ1 | SEQ ID NO: 9 |
| CELF4-F1 | aaaaaaaATGTAGTTTTTTTTTTTCG | SEQ ID NO: 10 |
| CELF4-R1 | tttttttATTTAAACTAAAAAAACG | SEQ ID NO: 11 |
| CELF4-FP1 | ROX-aatccAATGCGCGTTCGGATTTTCG-BHQ2 | SEQ ID NO: 12 |
| CELF4-F2 | attccatGTATATAAAGATGGTTACG | SEQ ID NO: 13 |
| CELF4-R2 | gattaagAACTATAACTTAATCCG | SEQ ID NO: 14 |
| CELF4-FP2 | ROX-atctaTAACGGGTTCGGTAGTAGTT-BHQ2 | SEQ ID NO: 15 |
| CELF4-F3 | cccaaaaTAAGATTGGGTTTTGGGCG | SEQ ID NO: 16 |
| CELF4-R3 | atttgaaCATCCCCATCTTTCAAATCG | SEQ ID NO: 17 |
| CELF4-FP3 | ROX-cttcTAGCGGGCGTCGATGAAGAGA-BHQ2 | SEQ ID NO: 18 |
| HAND2-F1 | attataaaAAATAATAGTATTTATAATCG | SEQ ID NO: 19 |
| HAND2-R1 | tgagttatCTATTTAAAATAACTCACG | SEQ ID NO: 20 |
| HAND2-FP1 | CY5-tcctcTGTTCGTTCGGAGGATTTA-BHQ2 | SEQ ID NO: 21 |
| HAND2-F2 | acaataaaaTTAAAAAGTTTTATTGTCG | SEQ ID NO: 22 |
| HAND2-R2 | gttttaaCAACTACATCTTTAAAACCG | SEQ ID NO: 23 |
| HAND2-FP2 | CY5-aaaaGTTCGAGGCGTCGTTTTGT-BHQ2 | SEQ ID NO: 24 |
| HAND2-F3 | ctattaatGGATTTAGAGTATTAATAGCG | SEQ ID NO: 25 |
| HAND2-R3 | tttggttATATAACTAATAACCAAACG | SEQ ID NO: 26 |
| HAND2-FP3 | CY5-caatTTCGTCGAATTGCGCG-BHQ2 | SEQ ID NO: 27 |
| HS3ST2-F1 | caaacacccATTAGGGTAGGGTGTTTGCG | SEQ ID NO: 28 |
| HS3ST2-R1 | tggtggggCTAAACACCCCCACCACG | SEQ ID NO: 29 |
| HS3ST2-FP1 | HEX-aaatTCGGCGCGATTTCGATTTGGA-BHQ1 | SEQ ID NO: 30 |
| HS3ST2-F2 | cccccactGTAAGAGAGTGGGGGCG | SEQ ID NO: 31 |
| HS3ST2-R2 | ttaggttaATTTAAAAAATAACCTAACG | SEQ ID NO: 32 |
| HS3ST2-FP2 | HEX-ccccCGGCGCGGGTTCGGGGATT-BHQ1 | SEQ ID NO: 33 |
| HS3ST2-F3 | aaaactacTTTTGGTTAGTAGTTTTCG | SEQ ID NO: 34 |
| HS3ST2-R3 | tagggttAAACTACTATAACCCTACG | SEQ ID NO: 35 |
| HS3ST2-FP3 | HEX-aaaaAGCGTTACGCGAGTTTTTTAG-BHQ1 | SEQ ID NO: 36 |
| GAPDH-F | AGGTTAAATATAGTTGTTGA | SEQ ID NO: 37 |
| GAPDH-R | CAACCCAAACCCCCAAC | SEQ ID NO: 38 |
| GAPDH-FP | Joe-TAGTTGGGGGTTTGGGTT-BHQ1 | SEQ ID NO: 39 |

Notes:
F stands for forward detection primer,
R stands for reverse detection primer, and
FP stands for detection probe.
In this table, the probe sequences shown have been labeled with fluorescent groups and quenching groups.

The components in the kit without sample pretreatment reagents are as follows:

| Component | Main ingredients |
|---|---|
| PCR reaction solution | 0.5-1 µL of methylation-specific Taq DNA polymerase at a concentration of 1 U/µL; 2-5 µL of dNTPs at a concentration of 10 mM; $Mg^{2+}$ 2-6 µL at a concentration of 2-5 mM; 5 µL of 10 × DNA polymerase buffer; purified water made up to 15 µL. |
| Mixed solution of primers and probes | CDO1 gene forward and reverse primers and probes, CELF4 gene forward and reverse primers and probes, HAND2 gene forward and reverse primers and probes, HS3ST2 gene forward and reverse primers, probes, GAPDH gene primers and probes. |
| Positive quality control | Genomic DNA fragments of different malignant tumor cell lines |
| Negative quality control | Purified water |

60 endometrial cancer samples with known and clear pathological information were selected: 15 cases were identified as endometrioid carcinoma, 15 cases were identified as endometrial mucinous carcinoma, 15 cases were identified as endometrial serous carcinoma, and 15 cases were identified as endometrial clear cell carcinoma; 40 cases were benign endometrial samples. The above samples were all obtained from the retained samples of cervical exfoliated cells.

I. Sample Methylation Pretreatment

The methylation pretreatment reagent for a sample includes a cell genomic DNA extraction reagent and a DNA bisulfate conversion reagent.

1. Using the company's self-developed genomic DNA extraction kit (nucleic acid extraction or purification reagents (Beijing OriginPoly Bio-Tec Co., LtD., Beijing Large-scale Medical Equipment Record No. 20210020)) as a cell genomic DNA extraction reagent, genomic DNA was extracted from the above-mentioned 100 samples of endometrial benign and malignant cervical exfoliated cells. At the same time, DNA quality was monitored. The total amount of DNA was between 4 µg-8 µg, and the OD260/280 was between 1.9-2.0, maintaining a good yield and purity.

2. Using the company's self-developed bisulfite conversion kit (methylation detection sample pretreatment kit (Beijing OriginPoly Bio-Tec Co., LtD., Beijing Large-scale Medical Equipment Record No. 20200110)) as the DNA bisulfite conversion reagent, bisulfite conversion was performed on the extracted DNA. Unmethylated cytosine (C) in DNA was converted to uracil (U), while methylated cytosine (C) remained unchanged. The converted bis-DNA was obtained. The conversion efficiency of bisulfite in this example is 99.8%, which is higher than most bisulfite conversion kits on the market.

II. Fluorescence Quantitative PCR Amplification of Bis-DNA

3. Formulation of PCR Reaction Solution and Mixed Solution of Primers and Probes PCR reaction solution (15 µL/person)

| Component | Adding amount/ person (µL) |
|---|---|
| DNA polymerase with methylation characteristics (1 U/µL) | 0.85 |
| dNTPs(10 mM) | 4 |
| $Mg^{2+}$ (2-5 mM) | 3 |

-continued

| Component | Adding amount/ person (µL) |
|---|---|
| 10 × DNA polymerase buffer | 1.5 |
| Purified water | Made up to 15 µL |

Mixed solution of primers and probes (5 µL/person)

| Component | Adding amount/ person (µL) |
|---|---|
| CDO1/CELF1/HAND2/HS3ST2-F (100 µM) | 0.2-0.8 |
| CDO1/CELF1/HAND2/HS3ST2-R (100 µM) | 0.2-0.8 |
| CDO1/CELF1/HAND2/HS3ST2-FP (100 µM) | 0.2-0.4 |
| GAPDH gene-F (100 µM) | 0.05 |
| GAPDH gene-R (100 µM) | 0.05 |
| GAPDH gene-FP (100 µM) | 0.05 |
| Purified water | Make up to 5 µL |

4. Adding Samples

5 µL of negative quality control, positive quality control and transformed Bis-DNA clinical samples were added to the above-mentioned system, respectively. PCR reaction was carried out and the conditions are: Pre-denaturation at 96° C. for 5 min; Denaturation at 94° C. for 15 s, annealing and extension at 60° C. for 35 s, 45 cycles; Keep at 25° C. for 10 min.

5. The Amplification Procedure is as Follows:

Step 1: Pre-denaturation at 96° C. for 5 min;
Step 2: Denaturation at 94° C. for 15 s, annealing and extension at 60° C. for 35 s, 45 cycles;
Step 3: 25° C., 10 min;

Signal collection, FAM, HEX, ROX, Joe and CY5 signals were collected at 60° C.

6. Interpretation of Results (1) the internal standard channel has an S-shaped amplification curve and Ct value≤32.2 means the result is valid;

(2) the ΔCt values of the 4 genes are:

$$\Delta Ct(CDO1)=Ct(CDO1)-Ct(GAPDH);$$

$$\Delta Ct(CELF4)=Ct(CELF4)-Ct(GAPDH);$$

$$\Delta Ct(HAND2)=Ct(HAND2)-Ct(GAPDH);$$

$$\Delta Ct(HS3ST2)=Ct(HS3ST2)-Ct(GAPDH).$$

(3) the threshold and performance (including specificity, sensitivity, negative predictive value, positive predictive value) of multiple methylated regions in the target genes were determined by integrating the ΔCt values of the above 4 genes and according to the ROC curve to determine the optimal methylated region and the interpretation method for the 4 target genes.

7. Analysis of Detection Results

A total of 100 samples were detected using the above kit reaction system, including 60 samples of endometrial cancer and 40 samples of benign endometrium.

Comparing the clinicopathological results, in 100 samples of cervical exfoliated cells, the positive rate of CDO1 (Chr5: 115816884-115817037) in endometrial cancer was 58.3% (35/60), the specificity in benign samples was 82.5% (33/40), and the ROC area was 0.728;

the positive rate of CDO1 (Chr5: 115816018-115816152) in endometrial cancer was 50% (30/60), the specificity in benign samples was 92.5% (37/40), and the ROC area was 0.714;

the positive rate of CDO1 (Chr5: 115815760-115815872) in endometrial cancer was 68.3% (41/60), the specificity in benign samples was 80% (32/40), and the ROC area was 0.767;

the positive rate of CELF4 (Chr18: 37566573-37566662) in endometrial cancer was 61.7% (37/60), the specificity in benign samples was 90% (36/40), and the ROC area was 0.776;

the positive rate of CELF4 (Chr18: 37565524-37565639) in endometrial cancer was 73.3% (44/60), the specificity in benign samples was 87.5% (35/40), and the ROC area was 0.847;

the positive rate of CELF4 (Chr18: 37565036-37565173) in endometrial cancer was 86.7% (52/60), the specificity in benign samples was 62.5% (25/40), and the ROC area was 0.792;

the positive rate of HAND2 (Chr4: 173530858-173530953) in endometrial cancer was 46.7% (28/60), the specificity in benign samples was 100% (40/40), and the ROC area was 0.742;

the positive rate of HAND2 (Chr4: 173530225-173530335) in endometrial cancer was 60% (36/60), the specificity in benign samples was 95% (38/40), and the ROC area was 0.811;

the positive rate of HAND2 (Chr4: 173528847-173528958) in endometrial cancer was 78.3% (47/60), the specificity in benign samples was 90% (36/40), and the ROC area was 0.882;

the positive rate of HS3ST2 (Chr16: 22813813-22813928) in endometrial cancer was 86.7% (52/60), the specificity in benign samples was 95% (38/40), and the ROC area was 0.915;

the positive rate of HS3ST2 (Chr16: 22814029-22814146) in endometrial cancer was 66.7% (40/60), the specificity in benign samples was 95% (38/40), and the ROC area was 0.790;

the positive rate of HS3ST2 (Chr16: 22814452-22814557) in endometrial cancer was 91.7% (55/60), the specificity in benign samples was 65% (26/40), and the ROC area was 0.797.

After comparative analysis of multiple methylated regions in CDO1, CELF4, HAND2 and HS3ST2, the methylated region selected in the CDO1 gene was Chr5: 115815760-115815872, the methylated region selected in the CELF4 gene was Chr18: 37565524-37565639, the methylated region selected in the HAND2 gene was Chr4: 173528847-173528958, the methylated region selected in the HS3ST2 was Chr16: 22813813-22813928.

According to each of the best methylated regions in CDO1, CELF4, HAND2 and HS3ST2, combined detection was performed. Two genes can be involved in interpretation, or three or four genes can be involved in interpretation and analysis at the same time, and the results in the following table can be obtained:

TABLE 1

Combined detection performance of two genes

| Combined detection of genes | CDO1, CELF4 | CDO1, HAND2 | CDO1, HS3ST2 | CELF4, HAND2 | CELF4, HS3ST2 | HAND2, HS3ST2 |
|---|---|---|---|---|---|---|
| Sensitivity (positive rate in endometrial cancer) (positive for any gene) | 88.3% (53/60) | 90% (54/60) | 95% (57/60) | 98.3% (59/60) | 98.3% (59/60) | 98.3% (59/60) |
| Specificity (specificity in a sample of benign endometrium) (positive for any gene) | 67.5% (27/40) | 70% (28/40) | 75% (30/40) | 77.5% (31/40) | 82.5% (33/40) | 85% (34/40) |
| Sensitivity (positive rate in endometrial cancer) (positive for two genes at the same time) | 53.3% (32/60) | 56.7% (34/60) | 60% (36/60) | 53.3% (32/60) | 61.7% (37/60) | 66.7% (40/60) |
| Specificity (specificity in a sample of benign endometrium) (positive for two genes at the same time) | 100% (40/40) | 100% (40/40) | 100% (40/40) | 100% (40/40) | 100% (40/40) | 100% (40/40) |

TABLE 2

Combined detection performance of three genes

| Combined detection of genes | CDO1, CELF4, HAND2 | CDO1, CELF4, HS3ST2 | CELF4, HAND2, HS3ST2 |
|---|---|---|---|
| Sensitivity (positive rate in endometrial cancer) (positive for any gene) | 98.3% (59/60) | 98.3% (59/60) | 98.3% (59/60) |
| Specificity (specificity in a sample of benign endometrium) (positive for any gene) | 57.5% (23/40) | 65% (26/40) | 72.5% (29/40) |
| Sensitivity (positive rate in endometrial cancer) (positive for any two genes) | 80% (48/60) | 86.7% (52/60) | 90% (54/60) |
| Specificity (specificity in a sample of benign endometrium) (positive for any two genes) | 100% (40/40) | 100% (40/40) | 100% (40/40) |

TABLE 2-continued

Combined detection performance of three genes

| Combined detection of genes | CDO1, CELF4, HAND2 | CDO1, CELF4, HS3ST2 | CELF4, HAND2, HS3ST2 |
|---|---|---|---|
| Sensitivity (positive rate in endometrial cancer) (positive for three genes at the same time) | 41.7% (25/60) | 48.3% (29/60) | 41.7% (25/60) |
| Specificity (specificity in a sample of benign endometrium) (positive for three genes at the same time) | 100% (40/40) | 100% (40/40) | 100% (40/40) |

TABLE 3

Combined detection performance of four genes

| Combined detection of genes | CDO1, CELF4, HAND2, HS3ST2 |
|---|---|
| Sensitivity (positive rate in endometrial cancer) (positive for any gene) | 98.3% (59/60) |
| Specificity (specificity in a sample of benign endometrium) (positive for any gene) | 52.5% (21/40) |
| Sensitivity (positive rate in endometrial cancer) (positive for any two genes) | 98.3% (59/60) |
| Specificity (specificity in a sample of benign endometrium) (positive for any two genes) | 100% (40/40) |
| Sensitivity (positive rate in endometrial cancer) (positive for any three genes at the same time) | 78.3% (47/60) |
| Specificity (specificity in a sample of benign endometrium) (positive for any three genes at the same time) | 100% (40/40) |
| Sensitivity (positive rate in endometrial cancer) (positive for four genes at the same time) | 66.7% (40/60) |
| Specificity (specificity in a sample of benign endometrium) (positive for four genes at the same time) | 100% (40/40) |

From the above table, we can see that when any two of the four genes are positive at the same time, the positive rate in endometrial cancer is 98.3% (59/60), the specificity in benign samples is 100% (40/40) and the ROC area detected is 0.990.

Therefore, through the analysis in Example 1, it can be concluded that the combined detection of CDO1, CELF4, HAND2, and HS3ST2 has the highest detection rate for endometrial cancer and has good specificity. Through the verification of a small amount of samples, the preliminary application of DNA methylation for the early detection of endometrial cancer is confirmed, and using cervical exfoliated cells can achieve high detection rate and very low false positive rate.

Example 2

Other components in the kit are the same as in Example 1. In Example 1, a small amount of single-center samples were tested, and then nearly 1,000 samples from multiple centers were collected for detection. The multiple centers include Peking Union Medical College Hospital, Peking University International Hospital, Chinese PLA General Hospital, Inner Mongolia People's Hospital, Hebei Cangzhou Central Hospital. Wherein 450 cases were endometrial cancer samples, 650 cases were benign endometrial samples, a total of 1,100 samples.

Comparing the histopathological and pathological results, the combined ROC curve area obtained by using this methylation detection kit was 0.98, the overall specificity was 98.5% (640/650), and the detection sensitivity for endometrial cancer was 98.9% (445/450).

The kit of the present invention, from verification using small amount of samples to research using large amount of samples, all prove that the use of DNA methylation for early detection of endometrial cancer has high accuracy and the detection can use only cervical exfoliated cells. The invention uses a special primer and probe design method and a sample pretreatment kit independently developed by the company. Multiple genes are used for combined detection and the functions are complementary. The detection of early endometrial cancer is significantly improved.

Herein, specific examples are used to describe the inventive concept in detail, and the description of the above embodiments is only used to help understand the core idea of the present invention. It should be pointed out that for those of ordinary skill in the art, any obvious modification, equivalent replacement or other improvement made should be included in the protection scope of the present invention without departing from the inventive concept.

The invention claimed is:

1. A composition comprising a set of detection primers for early screening and diagnosis of endometrial cancer, wherein the detection primers are useful to correspondingly detect methylation status of at least one methylated region in each of the target genes CDO1, CELF4, HAND2, and HS3ST2:
- wherein the detection primers for detecting methylation status of at least one methylated region of the CDO1-gene comprise SEQ ID NOs: 1 and 2, SEQ ID NOs: 4 and 5, or SEQ ID NOs: 7 and 8;
- wherein the detection primers for detecting methylation status of at least one methylated region of the CELF4 gene comprise SEQ ID NOs: 10 and 11, SEQ ID NOs: 13 and 14, or SEQ ID NOs: 16 and 17;
- wherein the detection primers for detecting methylation status of at least one methylated region of the HAND2 gene comprise SEQ ID NOs: 19 and 20, SEQ ID NOs: 22 and 23, or SEQ ID NOs: 25 and 26; and
- wherein the detection primers for detecting methylation status of at least one methylated region of the HS3ST2 gene comprise SEQ ID NOs: 28 and 29; SEQ ID NOs: 31 and 32, or SEQ ID NOs: 34 and 35,
- wherein each primer adopts a clasp structure and has added at its 5' end a sequence of 5-10 bp in length which is complementary to and pairs with the 3' end of the same primer to form a double-stranded binding region; and wherein the 5' end of the nucleotide sequence of each primer does not contain a CG site and the terminal last two bases at the 3' end of each primer are a CG dinucleotide.

2. The composition of claim 1, wherein:
(i) the detection primers for detecting methylation status of at least one methylated region of the CDO1 gene comprise SEQ ID NOs: 7 and 8;
(ii) the detection primers for detecting methylation status of at least one methylated region of the CELF4 gene comprise SEQ ID NOs: 13 and 14;
(iii) the detection primers for detecting methylation status of at least one methylated region of the HAND2 gene comprise SEQ ID NOs: 25 and 26; and
(iv) the detection primers for detecting methylation status of at least one methylated region of the HS3ST2 gene comprise SEQ ID NOs: 28 and 29.

3. A composition comprising a set of labeled detection probes for the detection of methylation status in each of the target genes CDO1, CELF4, HAND2, and HS3ST2:
- wherein the nucleotide sequence of the detection probe used to detect methylation status in the CDO1 gene is SEQ ID NO: 3, SEQ ID NO: 6 or SEQ ID NO: 9;
- wherein the nucleotide sequence of the detection probe used to detect methylation status in the CELF4 gene is SEQ ID NO: 12, SEQ ID NO: 15 or SEQ ID NO: 18;
- wherein the nucleotide sequence of the detection probe used to detect methylation status in the HAND2 gene is SEQ ID NO: 21, SEQ ID NO: 24 or SEQ ID NO: 27; and
- wherein the nucleotide sequence of the detection probe used to detect methylation status in the HS3ST2 gene is SEQ ID NO: 30, SEQ ID NO:33 or SEQ ID NO: 36,
- wherein the—nucleotide sequence of each detection—probe adopts a clasp structure and has added at its 5' end a sequence of 3-6 bp in length which is complementary to and pairs with the terminal 3-4 bp region near the 3' end of the same probe to form a double-stranded binding region; and wherein the 5' end of the nucleotide sequence of each probe does not contain a GC site; and
- wherein the 5' end of each—detection probe is labeled with a fluorescent group, and the 3' end is labeled with a quenching group, and the detection probe for each different target gene in the same detection system is labeled with a different fluorescent group.

4. The composition of claim 3, wherein:
(i) the nucleotide sequence of the detection probes used to detect methylation status in the CDO1 gene is SEQ ID NO: 9;
(ii) the nucleotide sequence of the detection probe used to detect methylation status in the CELF4 SEQ ID NO: 15;
(iii) the nucleotide sequence of the detection probe used to detect methylation status in the HAND2 gene is SEQ ID NO: 27; and
(iv) the nucleotide sequence of the detection probe used to methylation status in the HS3ST2 gene is SEQ ID NO: 30.

5. A kit for early screening and diagnosis of endometrial cancer, the kit comprising a set of detection primers of claim 1, and reagents and instructions therefor.

6. The kit of claim 5, wherein the set of detection primers comprises:
(i) detection primers for detecting methylation status of at least one methylation region of the CDO1-gene comprising SEQ ID NOs: 7 and 8;
(ii) detection primers for detecting methylation status of at least one methylation region of the CELF4 gene comprising SEQ ID NOs: 13 and 14;
(iii) detection primers for detecting methylation status of at least one methylation region of the HAND2 gene comprising SEQ ID NOs: 25 and 26; and
(iv) detection primers for detecting methylation status of at least one methylation region of the HS3ST2 gene comprising SEQ ID NOs: 28 and 29.

7. The kit of claim 5, further comprising a set of labeled detection probes to detect methylation status in each of the target genes CDO1, CELF4, HAND2, and HS3ST2:

wherein the nucleotide sequence of the detection probe used to detect methylation status in the CDO1 gene is SEQ ID NO: 3, SEQ ID NO: 6 or SEQ ID NO: 9;

wherein the nucleotide sequence of the detection probe used to detect methylation status in the CELF4 gene is SEQ ID NO: 12, SEQ ID NO: 15 or SEQ ID NO:18;

wherein the nucleotide sequence of the detection probe used to detect methylation status in the HAND2 gene is SEQ ID NO: 21, SEQ ID NO: 24 or SEQ ID NO: 27; and wherein the nucleotide sequence of the detection probe used to detect methylation status in the HS3ST2 gene is SEQ ID NO: 30, SEQ ID NO: 33 or SEQ ID NO:36, wherein the nucleotide sequence of each detection probe adopts a clasp structure and has added at its 5' end a sequence of 3-6 bp in length which is complementary to and pairs with the terminal 3-4 bp region near the 3' end of the same probe to form a double-stranded binding region; and wherein the 5' end of the nucleotide sequence of each detection probe does not contain a GC site.

8. The kit of claim 5, further comprising detection primers and a detection probe for an internal reference gene.

9. The kit of claim 8, wherein the internal reference gene is GAPDH.

10. The kit of claim 8, wherein the nucleotide sequences of the detection primers for the internal reference gene comprise SEQ ID NOs: 37 and 38.

11. The kit of claim 8, wherein the nucleotide sequence of the detection probe for the internal reference gene comprises SEQ ID NO: 39.

12. The kit of claim 8, wherein the 5' end of the nucleotide sequence of the detection probe for the internal reference gene is labeled with a fluorescent group and the 3' end is labeled with a quenching group; and/or wherein the 5' end of the nucleotide sequence of the detection probe for each target gene is labeled with a fluorescent group and the 3' end is labeled with a quenching group.

13. The kit of claim 12, wherein the fluorescent group for labeling the detection probe of the internal reference gene is different from the fluorescent group for labeling the detection probe of each target gene.

14. The kit of claim 5, further comprising at least one of:
(i) a PCR reaction solution; or
(ii) a methylation pretreatment reagent for a sample.

15. The kit of claim 14, wherein the sample comprises cervical exfoliated cells.

16. The kit of claim 14, wherein the methylation pretreatment reagent for the sample includes a cell genomic DNA extraction reagent and a DNA bisulfite conversion reagent.

17. The kit of claim 14, wherein the PCR reaction solution is packaged in single use units comprising 0.5-1 µL of methylation-specific Taq DNA polymerase at a concentration of 1 U/µL, 2-5 µL of dNTPs at a concentration of 10 mM, 2-6 µL of $Mg^{2+}$ at a concentration of 2-5 mM, 5 µL of 10×DNA polymerase buffer and purified water made up to 15 µL.

18. The kit of claim 7, wherein:
(i) the nucleotide sequence of the detection probe used to detect methylation status in the CDO1 gene is SEQ ID NO: 9;
(ii) the nucleotide sequence of the detection probe used to detect methylation status in the CELF4 is SEQ ID NO: 15;
(iii) the nucleotide sequence of the detection probe used to detect methylation status in the HAND2 gene is SEQ ID NO: 27; and
(iv) the nucleotide sequence of the detection probe used to methylation status in the HS3ST2 gene is SEQ ID NO: 30.

* * * * *

SEQUENCE LISTING

```
Sequence total quantity: 39
SEQ ID NO: 1            moltype = DNA  length = 29
FEATURE                 Location/Qualifiers
source                  1..29
                        mol_type = other DNA
                        organism = synthetic construct
                        note = based on Homo sapiens
SEQUENCE: 1
ctaaattttt ttttttttt tatttagcg                                              29

SEQ ID NO: 2            moltype = DNA  length = 27
FEATURE                 Location/Qualifiers
source                  1..27
                        mol_type = other DNA
                        organism = synthetic construct
                        note = based on Homo sapiens
SEQUENCE: 2
ttaaagtgtc tctcccccac tttaacg                                               27

SEQ ID NO: 3            moltype = DNA  length = 23
FEATURE                 Location/Qualifiers
source                  1..23
                        mol_type = other DNA
```

```
                       organism = synthetic construct
                       note = based on Homo sapiens
SEQUENCE: 3
tataattagc gtcgcgaatt ata                                            23

SEQ ID NO: 4          moltype = DNA   length = 25
FEATURE               Location/Qualifiers
source                1..25
                      mol_type = other DNA
                      organism = synthetic construct
                      note = based on Homo sapiens
SEQUENCE: 4
aaccaagttt aaagtgattg gttcg                                          25

SEQ ID NO: 5          moltype = DNA   length = 25
FEATURE               Location/Qualifiers
source                1..25
                      mol_type = other DNA
                      organism = synthetic construct
                      note = based on Homo sapiens
SEQUENCE: 5
aaggtccaat aaaatccacc ttccg                                          25

SEQ ID NO: 6          moltype = DNA   length = 21
FEATURE               Location/Qualifiers
source                1..21
                      mol_type = other DNA
                      organism = synthetic construct
                      note = based on Homo sapiens
SEQUENCE: 6
acccttagtc gcggggttgg t                                              21

SEQ ID NO: 7          moltype = DNA   length = 26
FEATURE               Location/Qualifiers
source                1..26
                      mol_type = other DNA
                      organism = synthetic construct
                      note = based on Homo sapiens
SEQUENCE: 7
ataacgttta tatttttaag ttatcg                                         26

SEQ ID NO: 8          moltype = DNA   length = 22
FEATURE               Location/Qualifiers
source                1..22
                      mol_type = other DNA
                      organism = synthetic construct
                      note = based on Homo sapiens
SEQUENCE: 8
gattagaccc tctactaatc cg                                             22

SEQ ID NO: 9          moltype = DNA   length = 26
FEATURE               Location/Qualifiers
source                1..26
                      mol_type = other DNA
                      organism = synthetic construct
                      note = based on Homo sapiens
SEQUENCE: 9
catctatttc gggcgcggag atgcgg                                         26

SEQ ID NO: 10         moltype = DNA   length = 27
FEATURE               Location/Qualifiers
source                1..27
                      mol_type = other DNA
                      organism = synthetic construct
                      note = based on Homo sapiens
SEQUENCE: 10
aaaaaaaatg tagttttttt tttttcg                                        27

SEQ ID NO: 11         moltype = DNA   length = 25
FEATURE               Location/Qualifiers
source                1..25
                      mol_type = other DNA
                      organism = synthetic construct
                      note = based on Homo sapiens
SEQUENCE: 11
tttttttatt taaactaaaa aaacg                                          25

SEQ ID NO: 12         moltype = DNA   length = 25
FEATURE               Location/Qualifiers
```

|   |   |   |
|---|---|---|
| source | 1..25<br>mol_type = other DNA<br>organism = synthetic construct<br>note = based on Homo sapiens | |
| SEQUENCE: 12 | | |
| aatccaatgc gcgttcggat tttcg | | 25 |
| SEQ ID NO: 13<br>FEATURE<br>source | moltype = DNA   length = 26<br>Location/Qualifiers<br>1..26<br>mol_type = other DNA<br>organism = synthetic construct<br>note = based on Homo sapiens | |
| SEQUENCE: 13 | | |
| attccatgta tataaagatg gttacg | | 26 |
| SEQ ID NO: 14<br>FEATURE<br>source | moltype = DNA   length = 24<br>Location/Qualifiers<br>1..24<br>mol_type = other DNA<br>organism = synthetic construct<br>note = based on Homo sapiens | |
| SEQUENCE: 14 | | |
| gattaagaac tataacttaa tccg | | 24 |
| SEQ ID NO: 15<br>FEATURE<br>source | moltype = DNA   length = 25<br>Location/Qualifiers<br>1..25<br>mol_type = other DNA<br>organism = synthetic construct<br>note = based on Homo sapiens | |
| SEQUENCE: 15 | | |
| atctataacg ggttcggtag tagtt | | 25 |
| SEQ ID NO: 16<br>FEATURE<br>source | moltype = DNA   length = 26<br>Location/Qualifiers<br>1..26<br>mol_type = other DNA<br>organism = synthetic construct<br>note = based on Homo sapiens | |
| SEQUENCE: 16 | | |
| cccaaaataa gattgggttt tgggcg | | 26 |
| SEQ ID NO: 17<br>FEATURE<br>source | moltype = DNA   length = 27<br>Location/Qualifiers<br>1..27<br>mol_type = other DNA<br>organism = synthetic construct<br>note = based on Homo sapiens | |
| SEQUENCE: 17 | | |
| atttgaacat ccccatctttt caaatcg | | 27 |
| SEQ ID NO: 18<br>FEATURE<br>source | moltype = DNA   length = 25<br>Location/Qualifiers<br>1..25<br>mol_type = other DNA<br>organism = synthetic construct<br>note = based on Homo sapiens | |
| SEQUENCE: 18 | | |
| cttctagcgg gcgtcgatga agaga | | 25 |
| SEQ ID NO: 19<br>FEATURE<br>source | moltype = DNA   length = 29<br>Location/Qualifiers<br>1..29<br>mol_type = other DNA<br>organism = synthetic construct<br>note = based on Homo sapiens | |
| SEQUENCE: 19 | | |
| attataaaaa ataatagtat ttataatcg | | 29 |
| SEQ ID NO: 20<br>FEATURE<br>source | moltype = DNA   length = 27<br>Location/Qualifiers<br>1..27<br>mol_type = other DNA<br>organism = synthetic construct<br>note = based on Homo sapiens | |
| SEQUENCE: 20 | | |
| tgagttatct atttaaaata actcacg | | 27 |

-continued

```
SEQ ID NO: 21           moltype = DNA   length = 24
FEATURE                 Location/Qualifiers
source                  1..24
                        mol_type = other DNA
                        organism = synthetic construct
                        note = based on Homo sapiens
SEQUENCE: 21
tcctctgttc gttcggagga ttta                                              24

SEQ ID NO: 22           moltype = DNA   length = 28
FEATURE                 Location/Qualifiers
source                  1..28
                        mol_type = other DNA
                        organism = synthetic construct
                        note = based on Homo sapiens
SEQUENCE: 22
acaataaaat taaaaagttt tattgtcg                                          28

SEQ ID NO: 23           moltype = DNA   length = 27
FEATURE                 Location/Qualifiers
source                  1..27
                        mol_type = other DNA
                        organism = synthetic construct
                        note = based on Homo sapiens
SEQUENCE: 23
gttttaacaa ctacatcttt aaaaccg                                           27

SEQ ID NO: 24           moltype = DNA   length = 24
FEATURE                 Location/Qualifiers
source                  1..24
                        mol_type = other DNA
                        organism = synthetic construct
                        note = based on Homo sapiens
SEQUENCE: 24
aaaagttcga ggcgtcgttt ttgt                                              24

SEQ ID NO: 25           moltype = DNA   length = 29
FEATURE                 Location/Qualifiers
source                  1..29
                        mol_type = other DNA
                        organism = synthetic construct
                        note = based on Homo sapiens
SEQUENCE: 25
ctattaatgg atttagagta ttaatagcg                                         29

SEQ ID NO: 26           moltype = DNA   length = 27
FEATURE                 Location/Qualifiers
source                  1..27
                        mol_type = other DNA
                        organism = synthetic construct
                        note = based on Homo sapiens
SEQUENCE: 26
tttggttata taactaataa ccaaacg                                           27

SEQ ID NO: 27           moltype = DNA   length = 20
FEATURE                 Location/Qualifiers
source                  1..20
                        mol_type = other DNA
                        organism = synthetic construct
                        note = based on Homo sapiens
SEQUENCE: 27
caatttcgtc gaattgcgcg                                                   20

SEQ ID NO: 28           moltype = DNA   length = 29
FEATURE                 Location/Qualifiers
source                  1..29
                        mol_type = other DNA
                        organism = synthetic construct
                        note = based on Homo sapiens
SEQUENCE: 28
caaacaccca ttagggtagg gtgtttgcg                                         29

SEQ ID NO: 29           moltype = DNA   length = 26
FEATURE                 Location/Qualifiers
source                  1..26
                        mol_type = other DNA
                        organism = synthetic construct
                        note = based on Homo sapiens
SEQUENCE: 29
```

```
tggtggggct aaacaccccc accacg                                              26

SEQ ID NO: 30             moltype = DNA   length = 25
FEATURE                   Location/Qualifiers
source                    1..25
                          mol_type = other DNA
                          organism = synthetic construct
                          note = based on Homo sapiens
SEQUENCE: 30
aaattcggcg cgatttcgat ttgga                                               25

SEQ ID NO: 31             moltype = DNA   length = 25
FEATURE                   Location/Qualifiers
source                    1..25
                          mol_type = other DNA
                          organism = synthetic construct
                          note = based on Homo sapiens
SEQUENCE: 31
cccccactgt aagagagtgg gggcg                                               25

SEQ ID NO: 32             moltype = DNA   length = 28
FEATURE                   Location/Qualifiers
source                    1..28
                          mol_type = other DNA
                          organism = synthetic construct
                          note = based on Homo sapiens
SEQUENCE: 32
ttaggttaat ttaaaaaata acctaacg                                            28

SEQ ID NO: 33             moltype = DNA   length = 24
FEATURE                   Location/Qualifiers
source                    1..24
                          mol_type = other DNA
                          organism = synthetic construct
                          note = based on Homo sapiens
SEQUENCE: 33
cccccggcgc gggttcgggg gatt                                                24

SEQ ID NO: 34             moltype = DNA   length = 27
FEATURE                   Location/Qualifiers
source                    1..27
                          mol_type = other DNA
                          organism = synthetic construct
                          note = based on Homo sapiens
SEQUENCE: 34
aaaactactt ttggttagta gttttcg                                             27

SEQ ID NO: 35             moltype = DNA   length = 26
FEATURE                   Location/Qualifiers
source                    1..26
                          mol_type = other DNA
                          organism = synthetic construct
                          note = based on Homo sapiens
SEQUENCE: 35
tagggttaaa ctactataac cctacg                                              26

SEQ ID NO: 36             moltype = DNA   length = 25
FEATURE                   Location/Qualifiers
source                    1..25
                          mol_type = other DNA
                          organism = synthetic construct
                          note = based on Homo sapiens
SEQUENCE: 36
aaaaagcgtt acgcgagttt tttag                                               25

SEQ ID NO: 37             moltype = DNA   length = 20
FEATURE                   Location/Qualifiers
source                    1..20
                          mol_type = other DNA
                          organism = synthetic construct
                          note = based on Homo sapiens
SEQUENCE: 37
aggttaaata tagttgttga                                                     20

SEQ ID NO: 38             moltype = DNA   length = 17
FEATURE                   Location/Qualifiers
source                    1..17
                          mol_type = other DNA
                          organism = synthetic construct
```

```
                    note = based on Homo sapiens
SEQUENCE: 38
caacccaaac ccccaac                                                    17

SEQ ID NO: 39       moltype = DNA  length = 18
FEATURE             Location/Qualifiers
source              1..18
                    mol_type = other DNA
                    organism = synthetic construct
                    note = based on Homo sapiens
SEQUENCE: 39
tagttggggg tttgggtt                                                   18
```